United States Patent [19]

Koprowski et al.

[11] 4,172,124

[45] Oct. 23, 1979

[54] METHOD OF PRODUCING TUMOR ANTIBODIES

[75] Inventors: Hilary Koprowski, Wynnewood; Carlo M. Croce, Philadelphia, both of Pa.

[73] Assignee: The Wistar Institute, Philadelphia, Pa.

[21] Appl. No.: 901,102

[22] Filed: Apr. 28, 1978

[51] Int. Cl.² ............... A61K 39/00; A61K 39/42; C12K 9/00
[52] U.S. Cl. ............................. 424/85; 424/86; 435/240; 435/172
[58] Field of Search ............... 424/85, 86; 195/1.8

[56] References Cited

PUBLICATIONS

Welsh-Nature, vol. 266, Apr. 1977, p. 495.
Galfre et al.-Nature, vol. 266, Apr. 1977, pp. 550-552.
Kohler et al.-Nature, vol. 256, Aug. 7, 1975, pp. 495-497.

*Primary Examiner*—Sam Rosen

[57] ABSTRACT

Antibodies demonstrating a specificity for malignant tumors are produced by somatic cell hybrids between hypoxanthine phosphoribosyltransferase deficient myeloma cells and spleen or lymph cells derived from an animal previously primed with tumor cells.

16 Claims, No Drawings

METHOD OF PRODUCING TUMOR ANTIBODIES

The invention described herein was made in the course of work under a grant or award from the Department of Health, Education and Welfare.

DESCRIPTION OF THE INVENTION

This invention relates to the production by living cells of antibodies specific for tumors and, more particularly, to the production of antibodies for tumors by fused cell hybrids.

Fused cell hybrids of spleen cells and myeloma cells have been described in the literature, inter alia, by Kohler et al in *Nature*, Vol. 256, 495–497 (1975) and *Eur. J. Immunol.*, Vol. 6, 511–519 (1976); by Milstein et al in *Nature*, Vol. 266, 550–552 (1977); and by Walsh, *Nature*, Vol. 266, 495 (1977). Prior to this invention, it was not known whether such hybrids, sometimes called hybridomas, could be formed that produced antibodies which were specific for tumors.

In accordance with this invention new cell lines have been propagated that produce large amounts of antibodies which exhibit a specificity for malignant tumors. The new cell lines are fused cell hybrids of (a) myeloma cells, i.e., malignant cells from primary tumors of bone marrow, and (b) antibody producing cells, preferably those of the spleen or lymph nodes of animals immunized with tumor cells. The fused cells are cultured and cloned, and clones which produce antibodies that demonstrate a specificity for tumor cells are selected. Antibodies may be recovered from the cultured hybrid although, at times, the entire culture may be employed if desired.

Following the practice of this invention, antibodies that demonstrate a specificity for tumor cells in either animals or man may be obtained. Importantly, the tumor cells for which antibodies may be obtained embrace human cancer cells, including, without limitation, melanoma, fibrosarcoma, breast carcinoma, lung carcinoma, colorectal carcinoma and uterus carcinoma. In some instances, for example in the case of SV40 induced tumors, the antibodies react with a nuclear antigen (e.g., the T antigen). In other cases, the antibodies can react with some component of the cell wall. Whatever the exact nature of the mechanism, it has been determined that an animal can be primed or immunized with tumor cells, and hybridomas derived from that animal will produce antibodies which demonstrate a specificity for the tumor.

Antibodies may be selected which exhibit a specificity that includes a given type of tumor within a species. The production of antibodies that react with tumors is of significant importance as an analytical tool as well as for diagnosis. It is also of importance for immunotherapy and for medical research.

The somatic cell hybrids of this invention are produced by fusing myeloma cells with anti tumor antibody producing cells. Myeloma cells are unique in that such cells are capable of producing antibodies albeit the specificity of these antibodies is as yet generally unknown. The anti tumor antibody producing cells are preferably spleen or lymph cells from animals that have been immunized (primed) with tumor cells. The particular species of animal from which the myeloma and spleen cells are derived is not critical insofar as it is possible to fuse the cells of the one species with another, i.e., mouse to rat, rat to human, or mouse to human. It is preferred, however, to use the same species of animal as a source of both myeloma and anti tumor antibody producing cells. One preferred cell line for the practice of this invention is a fused cell hybrid between tumor antigen primed mouse spleen cells and mouse myeloma cells. Excellent results have been obtained with somatic cell hybrids between the anti tumor antibody producing spleen cells of a BALB/c mouse previously immunized with tumor cells and myeloma cells of a BALB/c mouse. Particularly preferred myeloma cells are those of the MOPC-21 line called clone (P3×63 Ag8) and disclosed by Kohler et al in *Nature*, Vol. 256, 495–497 (1975).

After the cell lines have been fused, clones are grown from individual hybridizations and clones producing antibodies specific for tumor antigens are selected for antibody production. Since each hybridization does not result in the production of the same antibody, the antibodies produced by the individual clones will vary. Not all clones will produce antibodies for the tumor. In one study with SV40 tumor antigen, for example, less than 10% of the clones produced anti tumor antigen antibodies. Moreover, even among the clones that produced anti tumor antigen antibodies, the antibodies were produced in response to different antigen determinants. Some of the hybrids produced antibodies that cross-reacted with both SV40 tumor antigen and the related BK virus tumor antigen, whereas other hybrids produced antibodies that recognized SV40 tumor antigen but did not recognize BK tumor antigen. Similarly, anti tumor antibody producing clones can be selected that produce antibodies with varying degrees of selectivity for the tumor cells. Some may react only with cells of a specific tumor while others may react with more than one type of tumor. Such variation provides an important tool for medical research and in determining cross-reactive specificities among different types of cells.

The hybrid cells can be maintained in vitro or can be grown in vivo in a histocompatible animal or in athymic nude mice to accumulate large amounts of antibodies in the serum and ascitic fluid of the animal. The hybrids can be implanted or can be injected into the host. The antibodies may be recovered from the culture medium or from the serum or ascitic fluid of the animal by means known in the art. See, for example, Proc. Natl. Acad. Sci. USA, 75, pp. 1510–1514 (1978).

The following is one typical procedure for preparing a cell line of hybrid cells. Each of the steps is a known procedure. While this procedure refers to fusing myeloma cells of a BALB/c mouse with the spleen cells of BALB/c mice primed with tumor cells, the procedure may also be employed using other myeloma cells and other anti tumor antibody producing cells. Similarly, although the procedure is described utilizing a particular strain of tumor induced by Simian virus 40 (SV40), the cells of other tumors can also be used. Indeed, either tumor cells or cell fragments can be employed for the immunization. Cell suspension or cell fragment suspensions for injection readily can be prepared according to techniques well known in the art.

(a) Typical Preparation of Spleen Cells for Fusion

BALB/c mice are primed by intraperitoneal injections of at least about $1 \times 10^6$ tumor cells in standard suspension or in tissue culture media. In one method, the animals are hyperimmunized 4 to 11 times at about one week intervals. In another method, animals are immunized once and boosted a single time 2–4 weeks after immunization. In either method the mice are sacrificed from 2 to 6 days after the final injection and their spleen is taken. A spleen cell suspension was prepared in the manner taught by Gerhard et al, *Eur. J. Immunol.*, 5, 720-725 (1975). Red blood cells were lysed by incubation for 15 minutes at 4° C. in NH$_4$Cl (0.83%). The resulting cell suspension was washed by one centrifugation (800×g) through heat-inactivated calf serum and one centrifugation in protein-free medium (RPMI 1640, buffered with 7.5 mM HEPES, pH 7.2). The tumor antigen titer of the serum from the spleen donors will be generally above about 1:10.

(b) Preparation of Myeloma Cells for Fusion

BALB/c (P3×63 Ag8) myeloma cells derived from the MOPC-21 line and deficient in hypoxanthine phosphoribosyltransferase (HPRT E.C.2.4.2.8) as described by Milstein in *Nature*, Vol. 256, 495-497 (1975), are maintained in culture medium, for example, Eagle's minimal essential medium (MEM) containing 10% fetal calf and 10% horse serum. The growth of P3×63 Ag8 myeloma cells is inhibited by selective hypoxanthine-aminopterin-thymidine medium.

(c) Production of Hybrid Cells

Spleen cell suspensions are prepared in phosphate buffer saline (PBS), and depleted of erythrocytes by hypotonic shock. The spleen cells and myeloma cells are fused in the presence of polyethyleneglycol (PEG) 1000 as described in Koprowski et al, (1977) Proc. Nat. Acad. Sci. USA 74, 2985-2988. After fusion, cells are suspended in hypoxanthine/aminopterin/thymidine (HAT) selective medium which is described in Littlefield (1964) Science 145, 709-710, and seeded in flasks or individual wells of tissue culture plates.

Tumor Antigen Assay

Antigen assays are known in the art and may be used for the practice of this invention regarding tumor cells.

Expression of SV40 tumor antigen, for example, is detected by indirect immunofluorescence according to the procedure described in Pope et al (1964) *J. Exp. Med.* 120, 121-128. Acetone fixed cells are reacted with control mouse anti tumor antigen antiserum for 30 min., washed, then reacted with fluoresceine tagged rabbit anti-mouse immunogolbulin. A distinctive pattern of nuclear fluorescence indicates the presence of tumor antigen. The hybrid cells are tested for the production of anti tumor antigen antibody by substituting hybridoma culture fluids for the control anti tumor antiserum on test cells known to be tumor antigen positive. The anti tumor titer of a serum or culture fluid is the last dilution that gives 100% staining of nuclei of SV40 transformed cells. Culture fluids from P3×63 Ag8 mouse myeloma cells do not contain any anti-SV40 tumor antigen activity. In addition, sera and ascites from BALB/c mice carrying P3×63 Ag8 myeloma tumors are also negative for anti-SV40 antigen activity. BK virus tumor antigen is detected following the above procedures.

Presence of anti-tumor antigens may be detected by radioimmunoassay. Culture fluid or serum or ascitic fluid of mice injected with the hybrids are added to tumor cells. The bound antibodies are quantitated by an antiserum against mouse immunoglobulin which is labeled with I$^{125}$. See Cedurel and Croce, *J. Immunol.*, 118, No. 6, pp. 1951-1956, June 1977.

The following examples are included for illustrative purposes only and are not intended to limit the scope of the invention.

EXAMPLE I

HPRT deficient P3×63 Ag8 mouse myeloma cells were fused (PEG induced fusion) with spleen cells derived from BALB/c mice hyperimmunized with C57SV cells (series A17.2); with spleen cells derived from C57BL/6J mice immunized with C57SV cells (series A25.1) and with spleen cells derived from BALB/c mice immunized with MKSBu100 (series B16.1) as shown in Table 1. The abbreviations used in this example are as follows:

| Abbreviation | Description |
|---|---|
| LN-SV | SV40 transformed human fibroblasts |
| HT1080-6TG | human fibrosarcoma derived cells |
| HEK | human embryo kidney cells |
| F5-1 | SV40 transformed Syrian hamster fibroblasts |
| B1 | Syrian hamster fibroblasts |
| C57SV | SV40 transformed fibroblasts from mouse strain C57BL |
| C57MEF | C57BL embryonic fibroblasts |
| MKSBu100 | SV40 transformed BALB/c kidney cells |
| BALB MEF | BALB/c embryonic fibroblasts |
| BALB 3T3 | BALB/c embryonic fibroblasts |
| HKBK-DNA-4 | Syrian hamster kidney cells transformed by BK virus DNA |

Two to three weeks after fusion hybrid cells growin in HAT selective medium appeared and were subcultured weekly in HAT selective medium. One hundred and forty-six independent hybrid cell cultures from 20 different fusions were obtaind and were then tested for the production of antibodies specific for SV40 tumor antigen.

Only 13 of the 146 hybrid cell cultures, ten of which were independently derived from the same fusion experiment (B16.1), were found to produce antibodies against SV40 tumor antigen. As shown in Table 1, the antibodies produced by the hybridomas and a control mouse antiserum raised against SV40 tumor antigen reacted with SV40 transformed human, hamster and mouse cels, as determined by indirect immunofluorescence, but did not react with normal or malignant cells derived from these same species.

TABLE 1

| | Source of antibody | | | |
|---|---|---|---|---|
| Test Cells | Anti-T serum[1] | A25.1#1B3[2] | A17.2#1[3] | 16.1#1B2[4] |
| LN-SV | + | + | + | + |
| HT1080-6TG | − | − | − | − |
| HEK | − | − | − | − |
| F5-1 | + | + | + | + |
| B1 | − | − | − | − |
| C57SV | + | + | + | + |
| C57MEF | − | − | − | − |
| MKSBu100 | + | + | + | + |
| BALB MEF | − | − | − | − |
| BALB 3T3 | − | − | − | − |

[1] 1:100 dilution of control serum from SV40 immune mouse.
[2] undiluted culture fluid.
[3] 1:20 dilution of serum from animal bearing a tumor induced by A17.2#1 hybrid cells.
[4] undiluted culture fluid. All the anti SV40 T antigen antibody producing hybrids derived from the B16.1#1 fusion behaved in identical fashion on these test cells.

EXAMPLE II

In order to establish whether the antibodies produced by the hybridomas of Example I crossreact with the tumor antigen of BK virus, culture fluids derived from eleven different hybrid cells and the serum from a mouse injected with an additional hybrid cell line were tested for the presence of anti-SV40 and BK virus tumor antigen antibodies using SV40 transformed human cells (LN-SV) and BK virus DNA transformed hamster kidney cells (HKBK-DNA-4) as test cells. As shown in Table 2, only four of the hybridoma antibodies crossreacted with BK virus tumor antigen, although as in the case of the control serum, the intensity of the fluorescence was generally weaker. The fact that antibody production was triggered by different antigenic determinants, only some of which were common to both SV40 tumor antigen and BK virus tumor antigen is very useful in their immunological and biochemical characterization.

TABLE 2

| Source of antibodies[1] | Test Cells | |
|---|---|---|
| | LN-SV | HKBK-DNA-4 |
| Anti-T serum[2] | + | + |
| A17.2#1[3] | + | − |
| A25.1#1B3 | + | + |
| B16.1#1B2 | + | − |
| B16.1#1B6 | + | − |
| B16.1#1C1 | + | − |
| B16.1#C5 | + | − |
| B16.1#A2 | + | + |
| B16.1#A3 | + | − |
| B16.1#A5 | + | − |
| B16.1#C4 | + | + |
| B16.1#D2 | + | − |
| B16.1#D5 | + | + |

[1] except where noted, undiluted culture fluids from hybrid cultures were used for testing.
[2] 1:100 dilution of control serum from SV40 immune mouse.
[3] 1:20 dilution of serum from animal bearing a tumor induced by A17.2#1 hybrid cells. Culture cells from A17.2#1 tumor were found to produce anti SV40 T antigen antibodies that did not crossreact with BK virus T antigen.

EXAMPLE III

The hybridomas (at least about $10^5$ cells) were injected into a syngeneic host (i.e., the same strain of mouse from which the spleen cells were obtained). After allowing the injected cells to grow in the host for from about 4 to 8 weeks, the anti-SV40 antigen antibody titer of the serum and ascites were measured. Those titers, as well as the antibody titer of the culture fluid are shown in Table 3. As Table 3 deomonstrates, very high antibody titers were obtained.

TABLE 3

| Hybridomas | Culture Fluid | Titer Serum | Ascites |
|---|---|---|---|
| A25.1#B3 | 1:5 | 1:6400 | 1:3200 |
| B16.1#2A2 | 1:2 | ND* | ND |
| B16.1#2C4 | 1:10 | ND | ND |
| B16.1#2D5 | 1:2 | ND | ND |
| B16.1#1B6 | 1:20 | 1:6400 | 1:3200 |
| B16.1#1C5 | 1:10 | ND | 1:3200 |
| B16.1#2A3 | 1:5 | 1:6400 | ND |
| B16.1#1:2 | 1:2 ND | 1:100 | |
| A17.2#1** | negative | 1:50 | ND |

*ND mice were not injected with hybridoma cells
**This hybrid was originally a producer of anti-SV40 T antigen antibodies, but became gative following subculture.

EXAMPLE IV

Cells obtained from human melanomas and human colorectal carcinomas grown in tissue culture as disclosed in Cancer Research, 36, 4562–4569 (1976) and hybrid cultures between a human melanoma and mouse fibroblast cells (IT22) were used for immunization of mice. The mice were primed with a primary intraperitoneal injection of $3 \times 10^7$ live tumor cells and a secondary intravenous booster of $1 \times 10^6$ live tumor cells about 2 weeks later. Spleen cells from mice sacrificed about 3 days after the secondary booster were used to form hybrid cultures according to the typical procedure described above.

Of 29 hybrid cultures obtained after fusing of spleen cells from mice immunized with human melanoma cells, 9 secreted antibodies that reacted in radioimmunoassay with human melanoma. After mice were immunized with human colorectal carcinomas, 3 out of 8 cultures produced anti-colorectal carcinoma antibodies. The results of this work and the crossreactivity of antibodies produced are shown in Table 4. The numbers and letters appearing in the legends of the table refer to individuals.

TABLE 4

| Donors Immunized with: | Hybridoma No. | Results of RIA Against Cells of: | | | | | | | | | | | | |
|---|---|---|---|---|---|---|---|---|---|---|---|---|---|---|
| | | Melanoma | | | | | | Colo-rectal Carcinoma | | | | | Normal Human | | |
| | | 690 | 691 | 489 | 843 | 1614 | 1694 | 480 | 948 | 403 | 1116 | 337 | W138 | HEF | FS2 |
| | 2 | + | + | + | + | + | + | + | + | − | + | + | + | + | + |
| | 4 | + | + | + | + | + | + | − | + | − | − | − | + | + | + |
| | 5 | + | + | + | + | + | − | + | + | − | + | + | + | + | + |
| | 6 | + | + | + | + | + | + | − | − | − | + | + | − | − | − |
| 691 | 9* | + | + | − | + | + | − | + | + | − | − | + | + | + | + |
| Human | | | | | | | | | | | | | | | | |
| Melanoma | 11* | + | + | − | + | + | + | + | + | + | − | + | + | + | + |
| | 12* | + | + | + | + | + | + | + | + | − | + | + | + | + | + |
| | 13 | + | + | − | − | − | + | − | − | − | − | − | − | − | − |
| | 19* | + | + | + | − | + | − | − | − | − | − | − | + | − | − |
| | 2* | − | + | + | + | − | + | − | − | − | − | ND | − | − | − |
| 691 X | 4* | + | + | − | + | − | + | − | − | − | − | ND | − | − | − |
| IT22 | | | | | | | | | | | | | | | | |
| Hybrid | 6* | + | + | + | + | + | + | − | + | − | − | ND | + | + | + |
| | 1 | + | + | − | + | + | + | + | + | + | + | + | + | + | − |
| 480 | | | | | | | | | | | | | | | | |
| Human Colo- | 3 | − | − | − | − | ± | − | + | − | − | − | − | − | − | − |
| rectal | | | | | | | | | | | | | | | | |
| Carcinoma | 4 | + | + | + | + | + | + | − | + | + | + | + | + | + | + |

*Also reactive with 691X × IT22 Hybrid

As can be seen from Table 4, one anti-melanoma antibody producing hybridoma (#13) reacted only against melanoma but not against colorectal carcinoma or normal human cells. Still another (#6) reacted against all melanomas but no normal human cells. Two melanoma×IT22 hybridomas produced antibodies that reacted against some of the melanomas but not against colorectal carcinoma or normal human cells.

Growth of melanoma tumors in nude nice was suppressed by prior implantation of hybridomas producing anti-melanoma antibodies and sera obtained from these mice showed a 500–1000 fold increase in binding capacity to melanoma cells over tissue culture media.

While attempts to identify antigenic determinants for cancer cells have so far been generally unsuccessful, the production of hybrid cultures secreting antibodies against either human melanoma or colorectal carcinoma permits a consideration of crossreactive specificites between human tumor cells and normal cells. Indeed, the production of a spectrum of specific antibodies by anti tumor antibody producing hybridomas provides both a useful analytical and a useful diagnostic tool.

The antibodies produced by the hybridomas of this invention can be used as a diagnostic aid by screening a patient's blood or body fluid to determine if antigens characteristic of a malignant tumor are present. If the antigen is present, the patient can be given an injection of an antibody as an aid to react with the antigen.

We claim:

1. A method of producing malignant tumor antibodies comprising immunizing an animal with tumor cells, forming fused cell hybrids between antibody producing cells from said animal and myeloma cells, cloning said hybrids and selecting clones which produce antibodies that demonstrate a specificity for said tumor cells.

2. A method according to claim 1 wherein the tumor antibody producing cell is selected from the group consisting of spleen cells and lymph node cells.

3. A method according to claim 2 wherein the antibody producing cell is a spleen cell.

4. A method according to claim 1 wherein said animal is selected from the group consisting of mice and rats.

5. A method according to claim 1 wherein the animal is immunized with human cancer cells.

6. A method according to claim 4 wherein the cancer is a melanoma.

7. A method according to claim 4 wherein the cancer is a colorectal carcinoma.

8. A method according to claim 1 wherein the hybrid is cultured in a medium containing hypoxanthine-aminopterin-thymidine.

9. A method according to claim 1 wherein both the antibody producing cells and the myeloma cells are derived from mice.

10. The process of claim 1 wherein said hybrid is introduced into an animal selected from the group consisting of a histocompatible animal and athymic nude mice and cultured in vivo.

11. A method according to claim 1 wherein a mouse is immunized with tumor cells and a fused cell hybrid is formed between the spleen cells of said mouse and mouse myeloma cells.

12. The method according to claim 11 wherein said immunized mouse is a BALB/c mouse.

13. The method according to claim 11 wherein said tumor cells are melanoma cells.

14. The method according to claim 11 wherein said tumor cells are colo-rectal carcinoma.

15. The method according to claim 10 wherein the hybrid is cultured in a medium containing hypoxanthine-aminopterin-thymidene.

16. The process of claim 11 wherein said hybrid is introduced into an animal selected from the group consisting of a histocompatible animal and athymic nude mice and cultured in vivo.

* * * * *

UNITED STATES PATENT AND TRADEMARK OFFICE
CERTIFICATE OF CORRECTION

PATENT NO. : 4,172,124
DATED : October 23, 1979
INVENTOR(S) : Hilary Koprowski and Carlo M. Croce It is certified that error appears in the above-identified patent and that said Letters Patent are hereby corrected as shown below:

Col. 8, line 23, "vivo" should read — vitro —

Col. 8, line 40, "vivo" should read — vitro —

Signed and Sealed this

Eleventh Day of March 1980

[SEAL]

Attest:

SIDNEY A. DIAMOND

Attesting Officer

Commissioner of Patents and Trademarks